(12) United States Patent
Miyagawa et al.

(10) Patent No.: US 9,775,884 B2
(45) Date of Patent: Oct. 3, 2017

(54) SOLID FIBRINOGEN PREPARATION (75) Inventors: Shinichi Miyagawa, Kumamoto (JP); Tatsuya Araki, Kumamoto (JP); Tsutomu Hamuro, Kumamoto (JP); Mika Okuda, Kumamoto (JP); Hiroshi Kaetsu, Kumamoto (JP)

(73) Assignee: The Chemo-Sero-Therapeutic Research Institute, Kumamoto-shi (JP)

(*) Notice: Subject to any disclaimer, the term of this patent is extended or adjusted under 35 U.S.C. 154(b) by 1659 days.

(21) Appl. No.: 12/532,547

(22) PCT Filed: Mar. 21, 2008

(86) PCT No.: PCT/JP2008/055254
§ 371 (c)(1),
(2), (4) Date: Nov. 3, 2009

(87) PCT Pub. No.: WO2008/117746
PCT Pub. Date: Oct. 2, 2008

(65) Prior Publication Data
US 2010/0119563 A1    May 13, 2010

(30) Foreign Application Priority Data

Mar. 22, 2007  (JP) ................................ 2007-075380

(51) Int. Cl.
| A61K 38/36 | (2006.01) |
| A61K 31/198 | (2006.01) |
| A61K 38/38 | (2006.01) |
| A61K 38/48 | (2006.01) |
| A61L 24/10 | (2006.01) |
| A61L 31/04 | (2006.01) |
| A61K 38/45 | (2006.01) |
| A61K 38/57 | (2006.01) |

(52) U.S. Cl.
CPC .......... *A61K 38/363* (2013.01); *A61K 31/198* (2013.01); *A61K 38/38* (2013.01); *A61K 38/45* (2013.01); *A61K 38/4833* (2013.01); *A61K 38/57* (2013.01); *A61L 24/106* (2013.01); *A61L 31/046* (2013.01); *C12Y 203/02013* (2013.01); *C12Y 304/21005* (2013.01)

(58) Field of Classification Search
None
See application file for complete search history.

(56) References Cited

U.S. PATENT DOCUMENTS

| 4,414,976 A | 11/1983 | Schwarz et al. | |
| 4,650,678 A | 3/1987 | Fuhge et al. | |
| 4,909,251 A | 3/1990 | Seelich | |
| 5,407,671 A | 4/1995 | Heimburger et al. | |
| 7,550,567 B2* | 6/2009 | Metzner et al. | 530/382 |
| 7,714,107 B2* | 5/2010 | Yayon et al. | 530/381 |

FOREIGN PATENT DOCUMENTS

| CA | 1 182 444 | 2/1985 |
| EP | 0 090 997 A2 | 10/1983 |
| JP | 58-185162 | 10/1983 |
| JP | 59-80253 | 5/1984 |
| JP | 60-204725 | 10/1985 |
| JP | 63-24951 | 2/1988 |
| JP | 63-40546 | 8/1988 |
| JP | 2-36872 | 2/1990 |
| JP | 4-7328 | 2/1992 |
| JP | 8-151330 | 6/1996 |
| JP | 2004-248984 | 9/2004 |
| WO | 2004-064878 | 8/2004 |
| WO | 2005/113030 | 12/2005 |

OTHER PUBLICATIONS

New England Biolabs Amino acid Structures: 1 page total. Retrieved from the internet Sep. 6, 2013.*
Iyakuhin Tenkabutsu Jiten, first edition, Yakuji Nippo Ltd., "Polysorbate 80", Jan. 14, 1994, p. 123, (with English summary).
Gerhard Dickneite, et al., "A comparison of fibrin sealants in relation to their in vitro and in vivo properties", Pharma Medica, vol. 21, No. 9, 2003, pp. 105-118, with partial English translation.
Budavari, et al., "Entry 7742: The Merck Index", Merck Research Laboratories, (1996), p. 1308 (previously submitted on May 8, 2012, submitting more legible copy).
Extended European Search Report issued Mar. 28, 2012, in Patent Application No. 08722618.9.
Office Action as received in the corresponding Japanese Patent Application No. 2009-506319 dated Oct. 2, 2012 w/English Translation.
Office Action dated Nov. 28, 2016 issued in corresponding Indian patent application No. 6191/CHENP/2009.

* cited by examiner

*Primary Examiner* — Marsha Tsay
(74) *Attorney, Agent, or Firm* — Oblon, McClelland, Maier & Neustadt, L.L.P.

(57) ABSTRACT

A fibrinogen preparation is provided which has an improved solubility, may be prepared within a short time and may be used rapidly in clinical set-up. A solid fibrinogen preparation comprising as a main ingredient fibrinogen and further containing the following components: albumin; a nonionic surfactant; a basic amino acid or a salt thereof; and at least two amino acids or a salt thereof selected from an acidic amino acid or a salt thereof and a neutral amino acid or a salt thereof. The solid fibrinogen composition of the present invention may be held on a medical material to form a supporting material holding fibrinogen. Besides, the supporting material holding fibrinogen may be combined with a component comprising as a main ingredient thrombin to provide a fibrin adhesive.

20 Claims, 4 Drawing Sheets

SOLID FIBRINOGEN PREPARATION

TECHNICAL FIELD

The present invention relates to the field of a medical drug, specifically fibrinogen and a fibrinogen preparation as a component of a tissue adhesive. More specifically, the present invention relates to a solid fibrinogen preparation which comprises as a main ingredient fibrinogen and further contains albumin, a nonionic surfactant, a basic amino acid, and at least two amino acids selected from an acidic amino acid or a neutral amino acid and has an improved solubility, and a tissue adhesive using the same.

BACKGROUND ART

Fibrinogen is a very important coagulation factor which acts in the final stage of the blood coagulation cascade. Fibrinogen, e.g. upon activation of the coagulation system after an injury, is converted by thrombin from its soluble form into insoluble fibrin which plays an important role in hemostasis and wound healing.

Fibrinogen has importance in hemostasis and wound healing. For instance, fibrinogen has been used clinically as an intravenous dosage form in a replacement therapy against congenital and acquired fibrinogen deficiencies etc. to hamper a serious bleeding by increasing the fibrinogen level in blood. Additionally, in recent years, fibrinogen in admixture with thrombin is used in a surgery as an adhesive for substitute of suture of soft organs such as the liver and the spleen or as an auxiliary agent for the suture. Fibrinogen has also widely been applied in other clinical set-up.

Such a preparation, capable of adhering to a wound or a tissue surface, may enhance a tension strength of an adhesion site or a joined wound, may fully be absorbed within the living body and may promote the healing of wound.

As described in Patent reference 1, a method of the preparation of a tissue adhesive comprising fibrinogen and blood coagulation factor XIII (Factor XIII) is known. Factor XIII is activated by thrombin in the presence of calcium ion (activated Factor XIII). The activated Factor XIII forms a cross-link of isopeptide linkage between fibrin molecules, i.e. γ dimer, to thereby increase physical strength and stability of the fibrin clot. Therefore, the fibrin adhesive used widely as a tissue adhesive comprises a substantively necessary amount of Factor XIII irrespective of whether said Factor XIII is externally added as a purified Factor XIII or contained as a contaminant of materials while preparation of fibrinogen. The term "a substantively necessary amount of Factor XIII" as used herein refers to a concentration resulting in γ dimer (non-Patent reference 1).

A tissue adhesive is not stable in a form of a solution and thus is used in clinical practice in a dosage form of a frozen solution or a lyophilized powder. Therefore, a commercially available preparation has to be thawed or rehydrated before application, in either of which a lot of time is wasted.

Additionally, to obtain a sufficient adhesive action as a fibrin adhesive, it is necessary to dissolve fibrinogen in a high concentration. The higher the concentration of fibrinogen to be coagulated is, the more favorable. However, there was a problem that such a high-concentration fibrinogen solution is not suitable for use in a surgery of urgency since it takes a long time to make the solution from a lyophilized fibrinogen preparation. It is concerned that a prolonged preparation including dissolution of a lyophilized fibrinogen may adversely affect a patient.

Moreover, when a fibrinogen solution is prepared in a high concentration, rehydration of a lyophilized powder tends to result in bubbling. After the rehydration, the resulting fibrinogen solution is transferred into an applicator such as a syringe, but due to the bubbling, the preparation-time is further prolonged. Therefore, a preparation with an improved defoaming property is desired in a clinical practice.

Thus, medical doctors demand that the time for preparation is shortened because a quick availability is critically important especially at emergency including surgical procedure.

For the reasons described above, many attempts have been done to obtain a lyophilized product which has an improved rehydration time. For example, Patent reference 2 describes a method and procedure of improving the solubility of a lyophilized medicine by using an apparatus in combination with heating and stirring, which however is still insufficient for an improved rehydration time.

It is known that the solubility of a poorly soluble protein may be improved by addition of a certain additives. For example, Patent reference 3 discloses a lyophilized fibrinogen composition containing urea or a substance with a guanidine residue. Also, Patent reference 4 discloses a lyophilized fibrinogen composition containing at least one biologically compatible surfactant. However, in any commercially available preparations manufactured by any methods, it takes a lot of time to rehydrate a lyophilized powder and hence further improvement in the dissolution time is desired.

Patent reference 1: Japanese Patent Publication No. 63-40546
Patent reference 2: Canadian Patent 1,182,444
Patent reference 3: Japanese Patent Publication No. 4-7328
Patent reference 4: Japanese Patent Publication No. 2-36872
Non-patent reference 1: Dickneite, G., et al., Pharma Medica 21(9), p. 105-118 (2003)

DISCLOSURE OF THE INVENTION

Technical Problem to be Solved by the Invention

Under these circumstances, an object of the present invention is to provide a fibrinogen preparation which has a reduced preparation time and may quickly be used in clinical practice relative to the preparations using the prior art, and a tissue adhesive comprising the same.

The difficulty in attaining the above object is that a fibrinogen preparation may be used in like manner as the preparations using the prior art and the preparation time is still reduced.

Means for Solving the Problems

Thus, viewing the above problems, the present inventors have earnestly studied and as a result succeeded in reducing the rehydration time by combining albumin, a nonionic surfactant, a basic amino acid, and two or more amino acids selected from an acidic amino acid or a neutral amino acid in a composition comprising fibrinogen as a main ingredient to thereby complete the present invention.

The present invention, as a fibrinogen preparation which is stable in a solid state and has the reduced preparation time, included the following inventions.

(1) A solid fibrinogen preparation comprising fibrinogen as a main ingredient and further containing the following component:

(a) albumin;
(b) a nonionic surfactant;
(c) a basic amino acid or a salt thereof; and
(d) at least two amino acids or a salt thereof selected from an acidic amino acid or a salt thereof and a neutral amino acid or a salt thereof.

(2) The solid fibrinogen preparation according to the above (1) wherein said basic amino acid or a salt thereof is any of arginine or a salt thereof, and lysine or a salt thereof.

(3) The solid fibrinogen preparation according to the above (1) wherein said acidic amino acid or a salt thereof is any of glutamic acid, aspartic acid, or a salt thereof, said neutral amino acid or a salt thereof is any of isoleucine, leucine, glycine, alanine, serine, threonine, glutamine, or a salt thereof.

(4) The solid fibrinogen preparation according to the above (3) wherein said component (d) includes at least two amino acids or a salt thereof, selected from at least two of the following groups:
(d-1) glutamic acid or aspartic acid
(d-2) isoleucine or leucine
(d-3) glycine, alanine, serine, threonine or glutamine.

(5) The solid fibrinogen preparation according to any of the above (1) to (4) wherein a combination of said component (c) and component (d) is any of the following:
arginine, glutamic acid and isoleucine, or a salt thereof;
arginine, glutamic acid and glycine, or a salt thereof;
arginine, glycine and isoleucine, or a salt thereof;
arginine, isoleucine, glycine and glutamic acid, or a salt thereof;
lysine, isoleucine, glycine and glutamic acid, or a salt thereof;
arginine, leucine, glycine and glutamic acid, or a salt thereof;
arginine, isoleucine, alanine and glutamic acid, or a salt thereof;
arginine, isoleucine, serine and glutamic acid, or a salt thereof;
arginine, isoleucine, threonine and glutamic acid, or a salt thereof;
arginine, isoleucine, glutamine and glutamic acid, or a salt thereof;
arginine, isoleucine, glycine and aspartic acid, or a salt thereof.

(6) The solid fibrinogen preparation according to any of the above (1) to (5), which further comprises at least one selected from Factor XIII, sodium chloride, sodium citrate, or aprotinin.

(7) A fibrin adhesive which comprises the solid fibrinogen preparation according to any of the above (1) to (6) in combination with a component comprising thrombin as a main ingredient.

(8) A supporting material holding fibrinogen wherein the components of the solid fibrinogen preparation according to any of the above (1) to (6) are held onto a medical material.

(9) A fibrin adhesive which comprises the supporting material holding fibrinogen according to the above (8) in combination with a component comprising thrombin as a main ingredient.

Effects of the Invention

In accordance with the present invention, a solid fibrinogen preparation may be provided that is rehydrated to a liquid state in a shorter time than the preparations using the prior art. The fibrinogen preparation of the present invention, due to its reduced rehydration time, has an advantage that it may be used more quickly at emergency. Additionally, the fibrinogen preparation of the present invention has another advantage that, due to a defoaming effect of a surfactant, a reconstituted fibrinogen solution may be quickly sucked into an applicator to thereby further reduce the preparation time.

Moreover, the fibrinogen composition obtained by the present invention may preliminarily be held on a supporting material to provide a fibrinogen preparation which is directly applicable to an affected area without rehydration with a solution. The fibrinogen preparation of the present invention which is held on the supporting material may dissolve quickly with a slight amount of water on the applied area to thereby exert a strong adhesive force in a shorter time.

BEST MODE FOR CARRYING OUT THE INVENTION

The solid fibrinogen preparation of the present invention comprises fibrinogen as a main ingredient and a substantially necessary amount of albumin, a nonionic surfactant, a basic amino acid, and two or more amino acids selected from an acidic amino acid or a neutral amino acid in a suitable buffer solution such as a solution containing sodium chloride, trisodium citrate.

A concentration of fibrinogen comprised in the preparation of the present invention is preferably 40 mg/mL or more, more preferably 80 mg/mL or more.

Albumin contained in the preparation of the present invention is preferably serum albumin. Human serum albumin is preferred when the preparation of the present invention is applied to human. A concentration of albumin comprised in the preparation of the present invention is preferably 5 mg/mL or more. The upper limit of the concentration may suitably be decided based on the common knowledge in the art and include but not limited to 15 mg/mL.

A nonionic surfactant comprised in the preparation of the present invention includes a fatty acid surfactant such as sucrose fatty acid ester, sorbitan fatty acid ester, polyoxyethylene sorbitan fatty acid ester, fatty acid alkanolamide and the like, a higher alcohol surfactant such as polyoxyethylene alkyl ether, alkyl glycoside and the like, and an alkylphenol surfactant such as polyoxyethylene alkyl phenyl ether and the like. Among these, a suitable example is Tween-surfactant and Triton-surfactant. An example of these suitable nonionic surfactants includes polyoxyethylene(20) sorbitan monooleate (Tween80) and tyloxapol.

A concentration of said nonionic surfactant need to be over the critical micellar concentration of each surfactant and preferably is 0.1 mg/mL or more. The upper limit of the concentration may suitably be decided based on the common knowledge in the art and include but not limited to 0.5 mg/mL.

The basic amino acid comprised in the preparation of the present invention is selected from any of arginine or a salt thereof and lysine or a salt thereof.

For the acidic amino acid or the neutral amino acid comprised in the preparation of the present invention, two or more amino acids may be selected from an acidic amino acid such as glutamic acid, aspartic acid, or a salt thereof, or a neutral amino acid such as isoleucine, leucine, glycine, alanine, serine, threonine, glutamine, or a salt thereof.

In addition, for the said acidic amino acid or the neutral amino acid, at least two amino acids or a salt thereof may be selected from at least 2 of the following groups:
(1) glutamic acid, or aspartic acid;
(2) isoleucine, or leucine;
(3) glycine, alanine, serine, threonine, or glutamine.

Moreover, a preferred combination of said basic amino acid with said acidic amino acid or neutral amino acid includes the following:
arginine, glutamic acid and isoleucine, or a salt thereof;
arginine, glutamic acid and glycine, or a salt thereof;
arginine, glycine and isoleucine, or a salt thereof;
arginine, isoleucine, glycine and glutamic acid, or a salt thereof;
lysine, isoleucine, glycine and glutamic acid, or a salt thereof;
arginine, leucine, glycine and glutamic acid, or a salt thereof;
arginine, isoleucine, alanine and glutamic acid, or a salt thereof;
arginine, isoleucine, serine and glutamic acid, or a salt thereof;
arginine, isoleucine, threonine and glutamic acid, or a salt thereof;
arginine, isoleucine, glutamine and glutamic acid, or a salt thereof;
arginine, isoleucine, glycine and aspartic acid, or a salt thereof.

A concentration of each amino acid or a salt thereof comprised in the preparation of the present invention is preferably 2 mg/mL or more. In case of a particularly preferred combination of the amino acids, including arginine, isoleucine, glycine and glutamic acid, a concentration of each amino acids is preferably 3 mg/mL or more, 3 mg/mL or more, 2 mg/mL or more and 2.5 mg/mL or more, respectively. The upper limit of the concentration may suitably be decided based on the common knowledge in the art and include but not limited to 36 mg/mL, 13 mg/mL, 15 mg/mL, and 30 mg/mL, respectively.

Factor XIII may be added additionally to the fibrinogen preparation of the present invention in order to enhance the physical strength and stability of the fibrin clot. A concentration of Factor XIII comprised in the preparation of the present invention is such that the cross-link of isopeptide linkage between fibrin molecules, i.e. γ dimer, may be formed and is preferably e.g. 0.4 unit or more/mL of the preparation.

A method for preparing fibrinogen, albumin and Factor XIII used in the present invention is not particularly limited and includes e.g. separation from human blood or by genetic recombination technique.

Fibrinogen, a main ingredient of the preparation of the present invention, may be prepared by known methods, including, for example, cold ethanol precipitation combined with glycine that decreases solubility of fibrinogen (Blomback, B. and Blomback, M., Arkiv Kemi, 10, p. 415-443 (1956)), and glycine precipitation using glycine alone (Kazal, L. A. et al., Proc. Soc. Exp. Biol. Med., 113, p. 989-994 (1963)), and the like as reported. Alternatively, fibrinogen produced by genetic recombination technique may also be used.

Factor XIII may be prepared by known methods, including, for example, purification from plasma (Curtis, C G., Lorand, L., Methods Enzymol., 45, p. 177-191 (1976)) as reported. Alternatively, Factor XIII produced by genetic recombination technique may also be used.

The fibrinogen preparation of the present invention, in addition to being provided in a dosage form contained in a vial, may be held on a medical material to form a supporting material holding fibrinogen.

Specifically, a medical material may be soaked in the fibrinogen solution comprised of the composition of the present invention and then dried, e.g. by lyophilization, to produce a supporting material holding fibrinogen.

An example of said supporting material is not particularly limited insofar as it may medically be used and includes for example cellulose, a cellulose derivative, collagen, gelatin, polyglycolic acid, polylactic acid, glycolic acid-lactic acid copolymer, polyglutamic acid, amylose, and the like. The supporting material may be in the form including a fiber assembly such as monofilament, cotton, paper, nonwoven fabric, textile, and knit, film, sponge, and the like. A preferable example is a nonwoven fabric of polyglycolic acid, bioabsorbable material, as used in Examples in the specification.

Besides, the fibrinogen preparation and the supporting material holding fibrinogen of the present invention may not only be used alone but also in combination with a component comprising thrombin as a main ingredient to thereby form a biological adhesive (fibrin adhesive) for human and animal tissue that may broadly be applicable in the clinical set-up.

The present invention is explained in more detail by means of the following Test and Examples but is not limited thereto.

EXAMPLE

Test: Test and Method
(1) Preparation of the Fibrinogen Lyophilized Powder

Domestic frozen donation-plasma were thawed at low temperature and the resulting cryoprecipitate were treated by a combination of cold ethanol precipitation and glycine precipitation to produce fibrinogen. A fibrinogen solution for use in lyophilization was prepared by dissolving fibrinogen in a citric acid buffer solution containing sodium chloride and then adding each additives (prepared at ¼ of the final concentration). The resulting fibrinogen solution was subjected to aseptic filtration and each 12 mL was dispensed into final containers (glass bottles), which were then lyophilized and hermetically sealed.

(2) Rehydration Time

Rehydration time was determined as a time necessary for complete dissolution at 23 to 26° C. after 3 mL of the solvent ($H_2O$) was added to the lyophilized powder. For dissolving the lyophilized powder, the vial container containing the solvent was vigorously shook by hand. A content of a coagulable protein (fibrinogen) upon dissolution was set to 80 mg/mL to 90 mg/mL. Rehydration time was reported as a mean (±SD) of four measurements.

(3) Defoaming Time

Defoaming time was determined as a total time from the point when the lyophilized powder was dissolved and left to stand at room temperature until the bubble formed on dissolution disappeared and the surface of the fibrinogen solution appeared. Defoaming time was reported as a mean (±SD) of three measurements.

(4) Content of Coagulable Protein (Fibrinogen)

A content of coagulable protein (fibrinogen) was determined according to the tests for clottable protein content and purity, which is a test for itemized product and is described in Notification of the Welfare Ministry, "MINIMUM REQUIREMENTS FOR BIOLOGICAL PRODUCTS". Briefly, an amount of proteins precipitated upon addition of thrombin to samples is determined. Purity of the material used in Examples (a ratio of the amount of coagulable protein to total proteins) was 90% or more. A content of fibrinogen described in Examples was reported as a mean of two measurements.

(5) Preparation of a Fibrinogen Sheet

A fibrinogen sheet was prepared by soaking a sheet of polyglycolic acid (Gunze: Neoveil (registered trademark)), a sheet-shaped medical material, with a fibrinogen solution at 50 μL/cm$^2$, followed by lyophilization. A fibrinogen sheet was prepared such that it has a final concentration of fibrinogen of 80 mg/mL to 90 mg/mL when the fibrinogen sheet is rehydrated with 50 μL/cm$^2$ of saline.

(6) Saturation Time of the Fibrinogen Sheet with Saline

A saturation time was determined as a time (second) from dropwise addition of saline (200 μL) onto fibrinogen sheet (2×2 cm) to completion of absorption of saline into the sheet while left standing. A saturation time was reported as a mean (±SD) of three measurements.

(7) Tensile Strength Test

A tensile strength of the fibrinogen sheet was determined by the method described in ASTM (American Society for Testing and Materials) (F2258: Standard Test) with some modification. First, 2 sheets of pig dermis were obtained and fixed by fixtures separately (2.5×2.5 cm). Next, 300 μL of 30 U/mL thrombin was absorbed into the pig dermis sheets and a fibrinogen sheet (2.5×2.5 cm) was tucked between these dermis and left to stand for 1 to 5 min. After that, a tensile strength was determined while the pig dermis sheets were pulled upward and downward at 2 mm/min of a moving rate. A content of a coagulable protein (fibrinogen) upon dissolution was set to 80 mg/mL to 90 mg/mL.

(8) Other Reagents

As used in the following Examples, NaCl was purchased from Tomita pharmaceutical Co., Ltd. Trisodium citrate dihydrate, serine, threonine, glutamine, leucine, alanine and isoleucine were purchased from Wako Pure Chemical Industries, Ltd. Glycine, arginine monohydrochloride, sodium glutamate, sodium aspartate, lysine monohydrochloride and tyloxapol (Triton WR-1339) were purchased from nacalai tesque and Tween80 was purchased from NOF CORPORATION. Albumin was purified from domestic plasma donations at Juridical Foundation the Chemo-Sero-Therapeutic Research Institute.

Example 1: Rehydration Time Relative to Prior Art

A lyophilized fibrinogen powder was prepared comprising fibrinogen as a main ingredient, a substantively necessary amount of albumin, isoleucine or glycine for a neutral amino acid, arginine monohydrochloride for a basic amino acid, sodium glutamate for an acidic amino acid, and Tween80 or tyloxapol for a surfactant, and rehydration time was determined upon addition of the solvent.

A lyophilized fibrinogen powder composition of the present invention was prepared comprising, upon rehydration, 84 mg/mL or more of fibrinogen, 17.5 mg/mL of NaCl, 12 mg/mL of trisodium citrate dihydrate, 10 mg/mL of HSA (human serum albumin), 0.2 mg/mL of Tween80 or 0.3 mg/mL of tyloxapol, isoleucine, glycine, arginine monohydrochloride and sodium glutamate and a rehydration time was determined as described above. Besides, as a prior art, lyophilized powders were prepared by reference to fibrinogen compositions described in the instructions of commercially available fibrin glue adhesives (three kinds) and a rehydration time was determined in the same way for comparison with those of the composition of the present invention.

Figure 1:
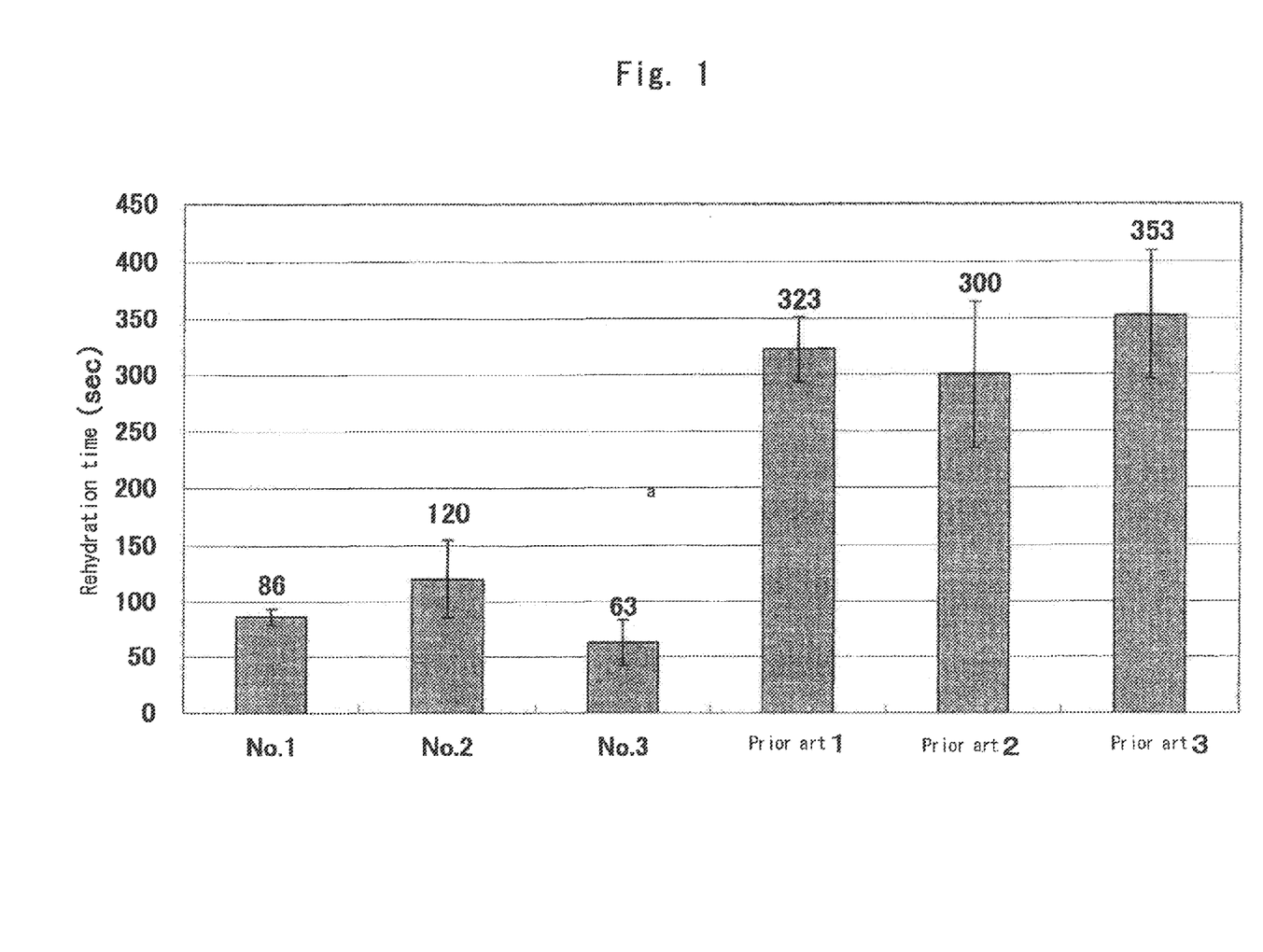
FIG. 1 is a graph comparing rehydration times of the fibrinogen compositions of the present invention and of the prior art.

Table 1 shows compositions, concentrations of each component, and a content of coagulable protein (fibrinogen) upon dissolution. In addition, FIG. 1 shows a rehydration time of the compositions of the present invention (No. 1 to No. 3) and the compositions based on prior art (Prior art 1 to Prior art 3). These results demonstrate that the composition of the present invention (No. 1 to No. 3) showed a significantly reduced rehydration time as compared to Prior art 1, Prior art 2 and Prior art 3 (cf. FIG. 1). Thus, it was proved that the composition of the present invention has an advantage over the prior art.

TABLE 1

| Additive | Composition Composition No | | | | | |
| --- | --- | --- | --- | --- | --- | --- |
| | No. 1 | No. 2 | No. 3 | Prior art 1 | Prior art 2 | Prior art 3 |
| NaCl(mg/mL) | 17.5 | 17.5 | 17.5 | 17.5 | 15 | 3 |
| Trisodium citrate (mg/mL) | 12 | 12 | 12 | 12 | 5 | 6 |
| Albumin (mg/mL): Al | 10 | 10 | 10 | 10 | 15 | 15 |
| Isoleucine (mg/mL): I | 4 | 4 | 13 | — | 13 | — |
| Glycine (mg/mL): G | 3 | 3 | 3 | 15 | — | 25 |
| Arginine monohydrochloride(mg/mL): R | 12 | 12 | 36 | — | 12 | — |
| Sodium glutamate (mg/mL): E | 10 | 10 | 10 | — | 10 | — |
| Mannitol (mg/mL) | — | — | — | 40 | — | — |
| Aprotinin (unit/mL) | — | — | — | — | — | 60 |
| Tween80(mg/mL): De | 0.2 | — | 0.2 | — | — | — |
| Tyloxapol (mg/mL): De | — | 0.3 | — | — | — | 0.3 |
| Content of Coagulable Protein (mg/mL) | 86 | 88 | 86 | 85 | 85 | 84 |

Example 2: Additives Required to Reduce Rehydration Time

There were prepared a lyophilized fibrinogen powder composition comprising, upon rehydration, 4 mg/mL of isoleucine (I), 2 mg/mL of glycine (G), 12 mg/mL of arginine monohydrochloride (R), 10 mg/mL of sodium glutamate (E), 10 mg/mL of HSA (human serum albumin: Al) and 0.2 mg/mL of Tween80(De) in addition to 84 mg/mL or more of fibrinogen, 17.5 mg/mL of NaCl and 12 mg/mL of trisodium citrate dihydrate (IGRE-AlDe) as well as lyophilized fibrinogen powder compositions comprising the composition of IGRE-AlDe with removal of any one of HSA, isoleucine, glycine, arginine monohydrochloride, sodium glutamate, or Tween80 (IGRE-De, GRE-AlDe, IRE-AlDe, IGE-AlDe, IGR-AlDe, and IGRE-Al, respectively). A rehydration time was determined as described above. Besides, as a prior art, the lyophilized fibrinogen powders of the compositions of Prior art 1 to Prior art 3 as used in Example 1 were prepared and a rehydration time was determined for comparison with those of the compositions as described above.

Figure 2:
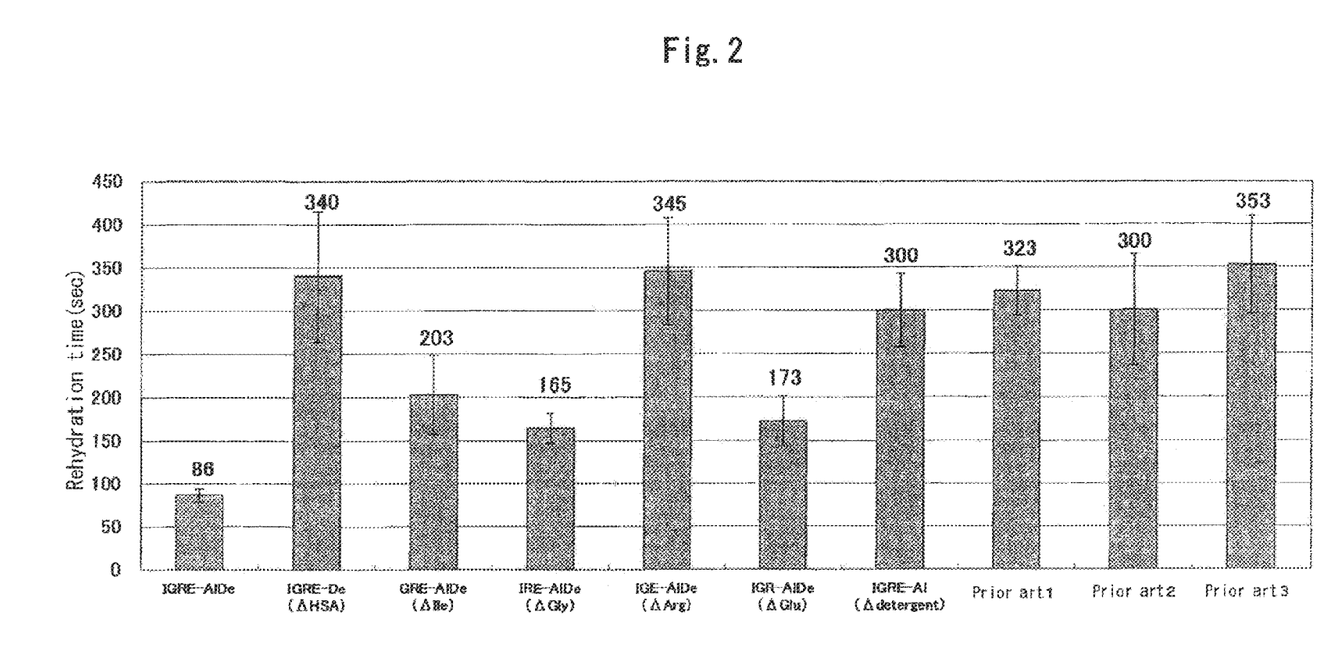
FIG. 2 is a graph showing the additives required for reducing rehydration time.

Table 2 shows compositions, concentrations of each component, and a content of coagulable protein (fibrinogen) upon dissolution. In addition, FIG. 2 shows measurements of rehydration time. As a result, it was demonstrated that IGRE-AlDe, GRE-AlDe, IRE-AlDe and IGR-AlDe were rehydrated in a shorter time than the prior art (Prior art 1 to 3) with IGRE-AlDe showing the shortest rehydration time. On the other hand, the rehydration time of IGRE-De, IGE-AlDe and IGRE-Al was similar to that of the preparation using the prior art. This demonstrates that, for achieving the reduced rehydration time of the present invention, albumin, arginine and a surfactant are essential and at least two of isoleucine, glycine, or glutamic acid are necessary.

Example 3: Rehydration Time on Replacement of Amino Acids

There were prepared a lyophilized fibrinogen powder composition comprising the composition, upon rehydration, of IGRE-AlDe as prepared in Example 2 as well as lyophilized fibrinogen powder compositions comprising the composition of IGRE-AlDe with replacement of each one of the four amino acids with other amino acids. A rehydration time was determined as described above. Besides, as a prior art, the lyophilized fibrinogen powder of the composition of Prior art 2 as used in Example 1 was prepared and a rehydration time was determined for comparison with those of the compositions of the present invention.

Compositions Comprising IGRE-AlDe with Replacement of Amino Acids

Replacement of Isoleucine (I):

Isoleucine (I) was replaced with leucine (L), a neutral amino acid (LGRE-AlDe).

Replacement of Glycine (G):

Glycine (G) was replaced with alanine (A), serine (S), threonine (T) or glutamine (Q), neutral amino acids (IARE-AlDe, ISRE-AlDe, ITRE-AlDe, IQRE-AlDe, respectively).

Replacement of Arginine (R):

Arginine (R) was replaced with lysine (K), classified as a basic amino acid likewise arginine (IGKE-AlDe).

Replacement of Glutamic Acid (E):

Glutamic acid (E) was replaced with aspartic acid (D), classified as an acidic amino acid likewise glutamic acid (IGRD-AlDe).

Figure 3:
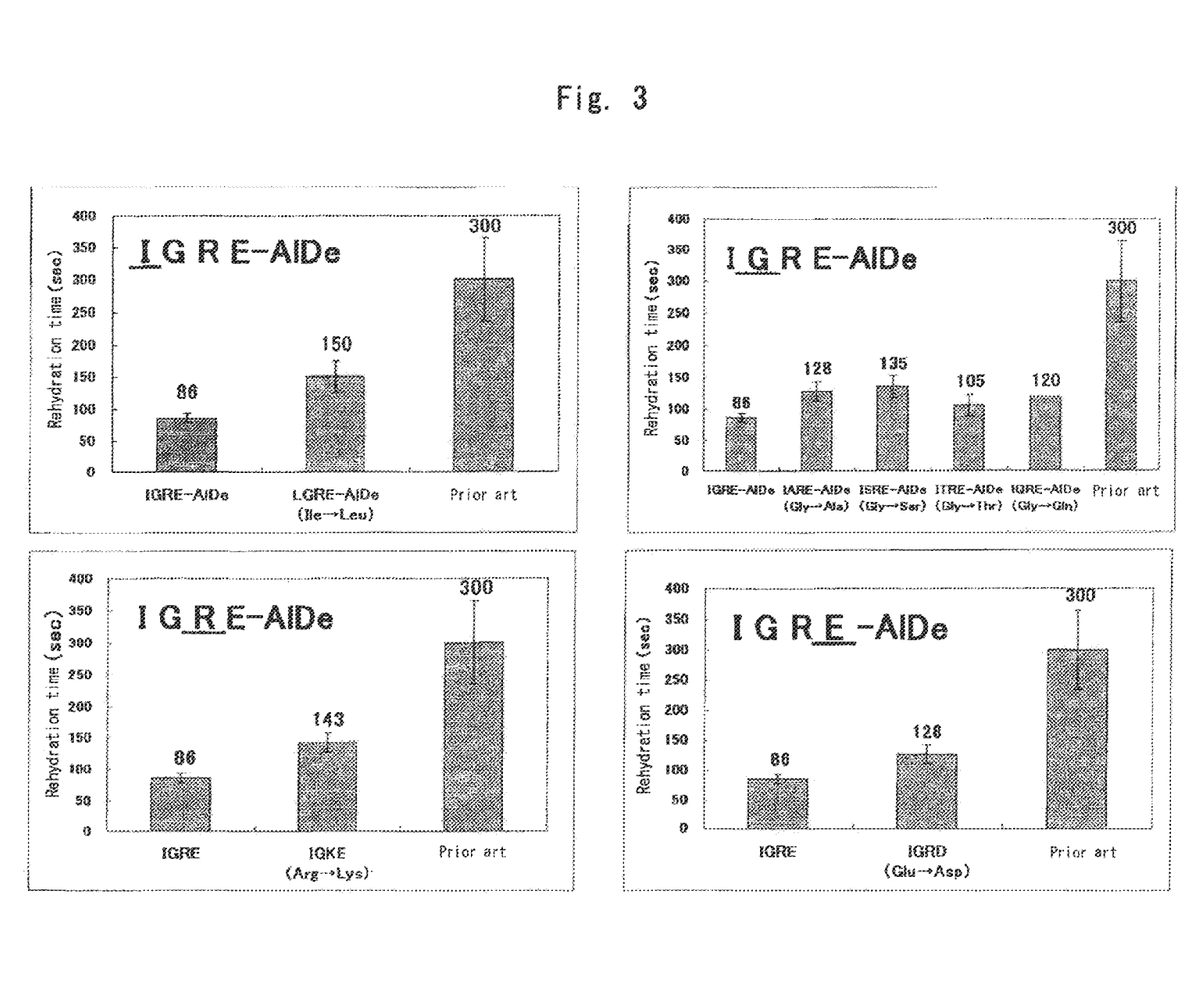
FIG. 3 includes graphs showing rehydration time of the fibrinogen composition of the present invention wherein each amino acid is replaced.

Table 3 shows compositions, concentrations of each component, and a content of coagulable protein (fibrinogen) upon dissolution. In addition, FIG. 3 shows the measurements of rehydration time. As a result, it was demonstrated that isoleucine could be replaced with leucine (FIG. 3, upper left), and that glycine could be replaced with alanine, serine, threonine and glutamine (FIG. 3, upper right). It was also demonstrated that arginine could be replaced with lysine (FIG. 3, lower left) and glutamic acid could be replaced with aspartic acid (FIG. 3, lower right). Table 4 shows those amino acids which were considered to be replaceable with each of the four amino acids. Thus, it was proved that the amino acids comprised in the lyophilized fibrinogen powder of the present invention are not limited to the four amino acids, i.e. isoleucine, glycine, arginine and glutamic acid, as described in tables 1 and 2 above, but may be any other amino acids having a similar property to these four amino acids.

TABLE 2

| Additive | IGRE-AlDe | IGRE-De (Δ HSA) | GRE-AlDe (Δ Ile) | IRE-AlDe (Δ Gly) | IGE-AlDe (Δ Arg) | IGR-AlDe (Δ Glu) | IGRE-Al (Δ detergent) | Prior art1 | Prior art2 | Prior art3 |
|---|---|---|---|---|---|---|---|---|---|---|
| NaCl(mg/mL) | 17.5 | 17.5 | 17.5 | 17.5 | 17.5 | 17.5 | 17.5 | 17.5 | 15 | 3 |
| Trisodium citrate(mg/mL) | 12 | 12 | 12 | 12 | 12 | 12 | 12 | 12 | 5 | 6 |
| Albumin(mg/mL): Al | 10 | — | 10 | 10 | 10 | 10 | 10 | 10 | 15 | 15 |
| Isoleucine(mg/mL): I | 4 | 4 | — | 4 | 4 | 4 | 4 | — | 13 | — |
| Glycine(mg/mL): G | 3 | 3 | 3 | — | 3 | 3 | 3 | 15 | — | 25 |
| Arginine monohydrochloride(mg/mL): R | 12 | 12 | 12 | 12 | — | 12 | 12 | — | 12 | — |
| Sodium glutamate(mg/mL): E | 10 | 10 | 10 | 10 | 10 | — | 10 | — | 10 | — |
| Mannitol(mg/mL) | — | — | — | — | — | — | — | 40 | — | — |
| Aprotinin(unit/mL) | — | — | — | — | — | — | — | — | — | 60 |
| Tween80(mg/mL): De | 0.2 | 0.2 | 0.2 | 0.2 | 0.2 | 0.2 | — | — | — | — |
| Tyloxapol(mg/mL): De | — | — | — | — | — | — | — | — | — | 0.3 |
| Content of Coagulable Protein(mg/mL) | 86 | 87 | 88 | 88 | 88 | 86 | 87 | 86 | 85 | 84 |

TABLE 3

| Additive | Composition |||||||||
|---|---|---|---|---|---|---|---|---|---|
| | IGRE-AlDe | LGRE-AlDe (Ile→Leu) | IARE-AlDe (Gly→Ala) | ISRE-AlDe (Gly→Ser) | ITRE-AlDe (Gly→Thr) | IQRE-AlDe (Gly→Gln) | IGKE-AlDe (Arg→Lys) | IGRD-AlDe (Glu→Asp) | Prior art |
| NaCl(mg/mL) | 17.5 | 17.5 | 17.6 | 17.5 | 17.5 | 17.5 | 17.5 | 17.5 | 15 |
| Trisodium citrate(mg/mL) | 12 | 12 | 12 | 12 | 12 | 12 | 12 | 12 | 5 |
| Albumin(mg/mL): Al | 10 | 10 | 10 | 10 | 10 | 10 | 10 | 10 | 15 |
| Isoleucine(mg/mL): I | 4 | — | 4 | 4 | 4 | 4 | 4 | 4 | 13 |
| Glycine(mg/mL): G | 3 | 3 | — | — | — | — | 3 | 3 | — |
| Arginine monohydrochloride(mg/mL): R | 12 | 12 | 12 | 12 | 12 | 12 | — | 12 | 12 |
| Sodium glutamate(mg/mL): E | 10 | 10 | 10 | 10 | 10 | 10 | 10 | — | 10 |
| Leucine(mg/mL): L | — | 4 | — | — | — | — | — | — | — |
| Alanine(unit/mL): A | — | — | 3 | — | — | — | — | — | — |
| Serine(unit/mL): S | — | — | — | 3 | — | — | — | — | — |
| Threonine(unit/mL): T | — | — | — | — | 3 | — | — | — | — |
| Glutamine(unit/mL): Q | — | — | — | — | — | 3 | — | — | — |
| Lysine monohydrochloride (unit/mL): K | — | — | — | — | — | — | 12 | — | — |
| Sodium aspartate(unit/mL): D | — | — | — | — | — | — | — | 10 | — |
| Tween80(mg/mL): De | 0.2 | 0.2 | 0.2 | 0.2 | 0.2 | 0.2 | 0.2 | 0.2 | — |
| Content of Coagulable Protein(mg/mL) | 86 | 88 | 88 | 88 | 87 | 87 | 86 | 87 | 85 |

TABLE 4

| | Neutral amino acid || Basic amino acid | Acidic amino acid |
|---|---|---|---|---|
| | Isoleucine | Glycine | Arginine | Glutamic acid |
| Replaceable | Leucine | Alanin Serine Threonine Glutamine | Lysine | Aspartic acid |

Example 4: Defoaming Effect with Surfactant

There were prepared a lyophilized fibrinogen powder composition comprising the composition, upon rehydration, of IGRE-AlDe as prepared in Example 2 as well as lyophilized fibrinogen powder compositions comprising the composition of IGRE-AlDe with removal of either Tween80 or one of the amino acids. A defoaming time upon rehydration was determined.

Table 5 shows compositions, concentrations of each component, a content of coagulable protein (fibrinogen) upon dissolution and a defoaming time. As a result, the defoaming could be detected around 2.5 to 6 min. for the compositions containing a surfactant: IGRE-AlDe, IGRE-AlDe (with replacement of Tween80 with tyloxapol), GRE-AlDe, IRE-AlDe and IGR-AlDe whereas the composition not containing surfactant IGRE-Al required 121 min. for defoamation. This demonstrated that the addition of a surfactant allowed for prompt extinction of foams resulting from rehydration of the lyophilized fibrinogen powder.

TABLE 5

| Additive | Composition ||||||
|---|---|---|---|---|---|---|
| | IGRE-AlDe | IGRE-AlDe (Tween80→ tyloxapol) | IGRE-Al (Δ Tween80) | GRE-AlDe (Δ Ile) | IRE-AlDe (Δ Gly) | IGR-AlDe (Δ Glu) |
| NaCl(mg/mL) | 17.5 | 17.5 | 17.5 | 17.5 | 17.5 | 17.5 |
| Trisodium citrate (mg/mL) | 12 | 12 | 12 | 12 | 12 | 12 |
| Albumin(mg/mL): Al | 10 | 10 | 10 | 10 | 10 | 10 |
| Isoleucine(mg/mL): I | 4 | 4 | 4 | — | 4 | 4 |
| Glycine(mg/mL): G | 3 | 3 | 3 | 3 | — | 3 |
| Arginine monohydrochloride(mg/mL): R | 12 | 12 | 12 | 12 | 12 | 12 |
| Sodium glutamate(mg/mL): E | 10 | 10 | 10 | 10 | 10 | — |
| Mannitol(mg/mL) | — | — | — | — | — | — |
| Aprotinin(unit/mL) | — | — | — | — | — | — |
| Tween80(mg/mL): De | 0.2 | — | — | 0.2 | 0.2 | 0.2 |
| Tyloxapol(mg/mL): De | — | 0.3 | — | — | — | — |
| Content of Coagulable Protein (mg/mL) | 86 | 86 | 84 | 88 | 88 | 86 |
| Defoaming time (Mean ± SD min) | 5.3 ± 2.5 min | 2.3 ± 0.6 min | 121.0 ± 14.7 min | 4.0 ± 2.0 min | 6.0 ± 1.0 min | 4.7 ± 0.6 min |

Example 5: Saturation Property and Tensile Strength of Fibrinogen Sheet

The fibrinogen solutions of the composition of IGRE-AlDe prepared in Example 2, of the composition of IGRE-AlDe with removal of isoleucine or glutamic acid (GRE-AlDe, IGR-AlDe, respectively) and of the composition of a commercially available fibrin glue adhesive (Prior art to 3) were used to prepare fibrinogen sheets and a saturation time and a tensile strength were determined.

Figure 4:
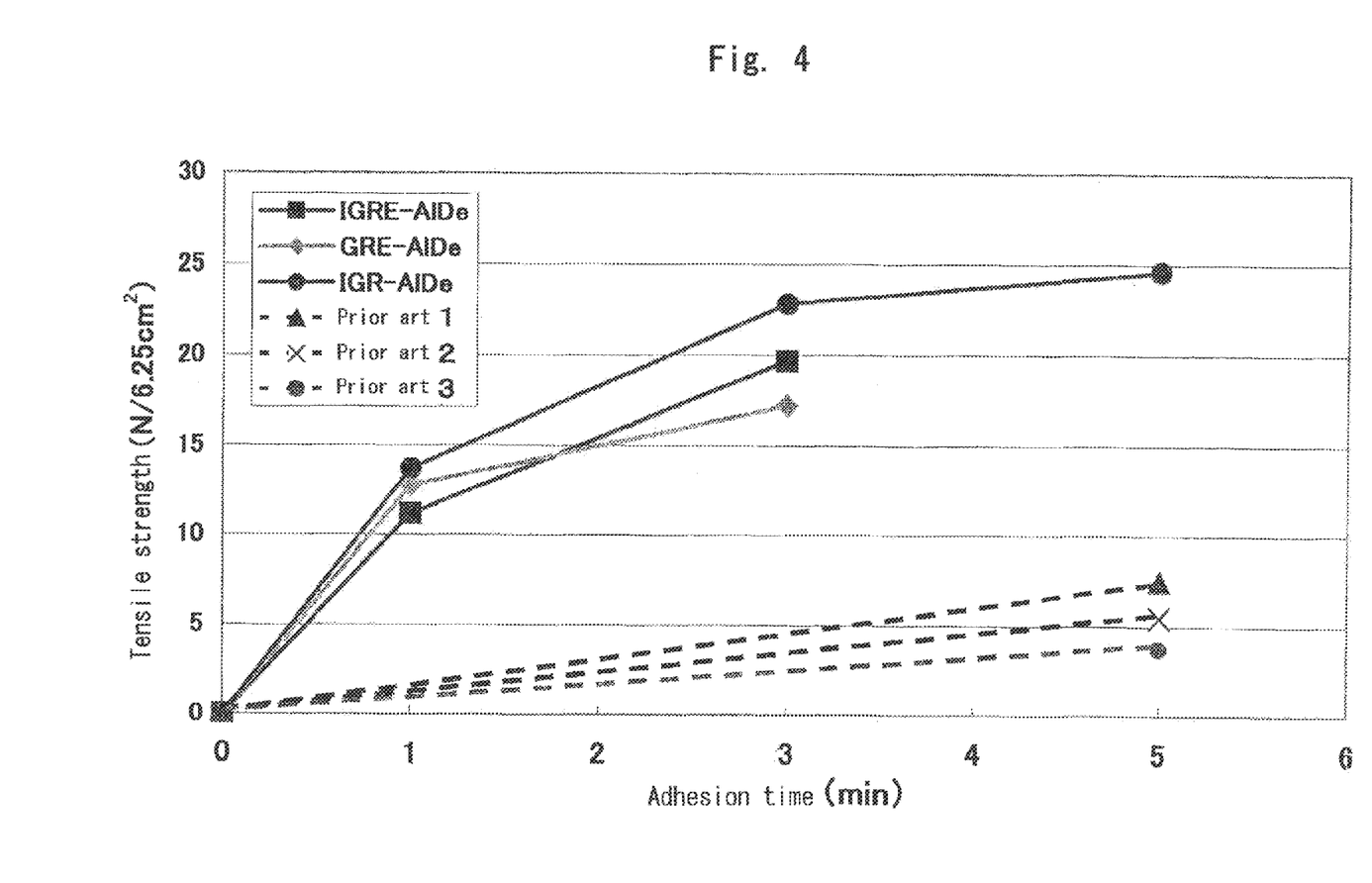
FIG. 4 is a graph comparing tensile strengths of the fibrinogen compositions of the present invention and of the prior art.

Table 6 shows compositions, concentrations of each component upon addition of saline and a saturation time. In addition, FIG. 4 shows the results of the tensile strength test. AS a result, as compared to prior art (Prior art 1 to 3), the fibrinogen sheets prepared using the compositions of the present invention (IGRE-AlDe, GRE-AlDe, IGR-AlDe) were saturated with saline in an extremely shorter time and provided a higher tensile strength.

These results prove that, in fact, a potent adhesion could be obtained without the procedure of dissolution of a lyophilized powder in a solution, which has commonly been used in the prior art. Thus, it is expected that the use of the solid fibrinogen preparation comprising the composition of the present invention allows for provision of a preparation capable of exerting a potent adhesion in a short time.

TABLE 6

| Additive | Composition IGRE-AlDe | Composition GRE-AlDe (Δ Ile) | Composition IGR-AlDe (Δ Glu) | Prior art 1 | Prior art 2 | Prior art 3 |
| --- | --- | --- | --- | --- | --- | --- |
| NaCl(mg/mL) | 17.5 | 17.5 | 17.5 | 18 | 15 | 3 |
| Trisodium citrate(mg/mL) | 12 | 12 | 12 | 12 | 5 | 6 |
| Albumin(mg/mL): Al | 10 | 10 | 10 | 10 | 15 | 15 |
| Isoleucine(mg/mL): I | 4 | — | 4 | — | 13 | — |
| Glycine(mg/mL): G | 3 | 3 | 3 | 15 | — | 25 |
| Arginine monohydrochloride(mg/mL): R | 12 | 12 | 12 | — | 12 | — |
| Sodium glutamate(mg/mL): E | 10 | 10 | — | — | 10 | — |
| Mannitol(mg/mL) | — | — | — | 40 | — | — |
| Aprotinin(unit/mL) | — | — | — | — | — | 60 |
| Tween80(mg/mL): De | 0.2 | 0.2 | 0.2 | — | — | — |
| Tyloxapol(mt/mL): De | — | — | — | — | — | 0.3 |
| Saturation time (Mean ± SD sec) | 6.5 ± 1.0 sec | 8.9 ± 4.1 sec | 9.0 ± 0.9 sec | 600 sec or more | 600 sec or more | 600 sec or more |

INDUSTRIAL APPLICABILITY

In accordance with the present invention, a solid fibrinogen preparation may be provided that is rehydrated to a liquid state in a shorter time than the preparations using the prior art. The fibrinogen preparation of the present invention, due to its reduced rehydration time, has an advantage that it may be used more quickly at emergency. Additionally, the fibrinogen preparation of the present invention has another advantage that, due to a defoaming effect of a surfactant, a reconstituted fibrinogen solution may be quickly sucked into an applicator to thereby further reduce the preparation time.

Moreover, the fibrinogen composition obtained by the present invention may preliminarily be held on a supporting material to provide a fibrinogen preparation which is directly applicable to an affected area without rehydration with a solution. The fibrinogen preparation of the present invention which is held on the supporting material may dissolve quickly with a slight amount of water on the applied area to thereby exert a strong adhesive force in a shorter time.

The invention claimed is:

1. A solid fibrinogen composition comprising fibrinogen, albumin, a non-ionic surfactant and a combination of amino acid or amino acid salts selected from the group consisting of:
   isoleucine, glycine, arginine, and glutamic acid, or salts thereof (IGRE);
   glycine, arginine, and glutamic acid, or salts thereof (GRE);
   isoleucine, glycine, and arginine, or salts thereof (IGR);
   leucine, glycine, arginine, and glutamic acid, or salts thereof (LGRE);
   isoleucine, alanine, arginine, and glutamic acid, or salts thereof (IARE);
   isoleucine, serine, arginine, and glutamic acid, or salts thereof (ISRE);
   isoleucine, threonine, arginine, and glutamic acid, or salts thereof (ITRE);
   isoleucine, glutamine, arginine, and glutamic acid, or salts thereof (IQRE); and
   isoleucine, glycine, lysine and glutamic acid, or salts thereof (IGKE).

2. The solid fibrinogen composition of claim 1, wherein the surfactant is tyloxapol or polysorbate 80.

3. The solid fibrinogen composition of claim 1, further comprising at least one of a monofilament, cotton, paper, cellulose, cellulose derivative, nonwoven fabric, textile, knit, sponge, film or other supporting material.

4. The solid composition of claim 1, further comprising at least one of collagen, gelatin, polyglycolic acid, polylactic acid, glycolic acid-lactic acid copolymer, polyglutamic acid, or amylose.

5. The solid fibrinogen composition of claim 1 in a lyophilized form and suitable for medical use.

6. A liquid composition produced by contacting water with the solid fibrinogen composition of claim 1.

7. The liquid composition of claim 6 that rehydrates faster or that has a shorter defoaming time than an otherwise identical composition produced by contacting water with a solid fibrinogen composition that does not contain at least one of albumin, a non-ionic surfactant, or one of the amino acids or amino acid salts in the combination of amino acids or amino acid salts.

8. A solid fibrinogen composition comprising fibrinogen, albumin, a non-ionic surfactant, and a combination of amino acids or amino acid salts selected from the group consisting of:
glycine or a glycine salt, arginine or a salt of arginine, glutamic acid or a salt of glutamic acid (GRE); and
isoleucine or an isoleucine salt, glycine or a glycine salt, arginine or a salt of arginine, (IGR).

9. The solid fibrinogen composition of claim 8, wherein the surfactant is tyloxapol or polysorbate 80.

10. The solid fibrinogen composition of claim 8, further comprising at least one of a monofilament, cotton, paper, cellulose, cellulose derivative, nonwoven fabric, textile, knit, sponge, film or other supporting material.

11. The solid fibrinogen composition of claim 8, further comprising at least one of collagen, gelatin, polyglycolic acid, polylactic acid, glycolic acid-lactic acid copolymer, polyglutamic acid, or amylose.

12. The solid fibrinogen composition of claim 8 in a lyophilized form and suitable for medical use.

13. A liquid composition produced by contacting water with the solid fibrinogen composition of claim 8.

14. The liquid composition of claim 13 that rehydrates faster or that has a shorter defoaming time than an otherwise identical composition produced by contacting water with a solid fibrinogen composition that does not contain at least one of albumin, a non-ionic surfactant, or one of the amino acids or amino acid salts in the combination of amino acids or amino acid salts.

15. A solid fibrinogen composition comprising fibrinogen, albumin, a non-ionic surfactant, and isoleucine or an isoleucine salt, glycine or a glycine salt, arginine or a salt of arginine, glutamic acid or a salt of glutamic acid (IGRE).

16. The solid fibrinogen composition of claim 15, wherein the surfactant is tyloxapol or polysorbate 80.

17. The solid fibrinogen composition of claim 15, further comprising at least one of a monofilament, cotton, paper, cellulose, cellulose derivative, nonwoven fabric, textile, knit, sponge, film or other supporting material.

18. The solid fibrinogen composition of claim 15, further comprising at least one of collagen, gelatin, polyglycolic acid, polylactic acid, glycolic acid-lactic acid copolymer, polyglutamic acid, or amylose.

19. A liquid composition produced by contacting water with the solid fibrinogen composition of claim 15.

20. The liquid composition of claim 19 that rehydrates faster or that has a shorter defoaming time than an otherwise identical composition produced by contacting water with a solid fibrinogen composition that does not contain at least one of albumin, a non-ionic surfactant, isoleucine or an isoleucine salt, glycine or a glycine salt, arginine or a salt of arginine, or glutamic acid or a salt of glutamic acid.

* * * * *